United States Patent [19]
Volk

[11] Patent Number: 4,627,694
[45] Date of Patent: Dec. 9, 1986

[54] INDIRECT OPHTHALMOSCOPY LENS FOR USE WITH SLIT LAMP BIOMICROSCOPE

[76] Inventor: David Volk, 3366 Kersdale Rd., Pepper Pike, Ohio 44124

[21] Appl. No.: 727,764

[22] Filed: May 1, 1985

[51] Int. Cl.$^4$ ............ A61B 3/14; A61B 3/10; G02B 13/18
[52] U.S. Cl. .................. 351/214; 351/205; 350/432; 350/435
[58] Field of Search ............ 351/205, 214; 350/432, 350/435

[56] References Cited

U.S. PATENT DOCUMENTS 3,781,097 12/1973 Bechtold ............................. 350/432

FOREIGN PATENT DOCUMENTS 880476 10/1961 United Kingdom ................ 350/432

Primary Examiner—Rodney B. Bovernick
Attorney, Agent, or Firm—Baldwin, Egan & Fetzer

[57] ABSTRACT

A very strong plus symmetrical double aspheric lens is used as a condensing-image-forming lens for indirect ophthalmoscopy with the slit lamp biomicroscope. The patient is seated at the slit lamp biomicroscope with his head held firmly in position by the chin rest and head support. The light beam from the slit lamp, with its slit open fully, is directed at the indirect ophthalmoscopy lens of this invention which converges the light beam to an image of the light source at or near the center of the pupil of the eye. The light beam then diverges to illuminate the fundus of the eye. An inverted aerial image of the fundus of the eye is then formed by the lens of this invention of the light emerging from the eye and is viewed monocularly or binocularly and stereoscopically with the binocular biomicroscope of the slit lamp which can magnify the aerial image from 7 to 40 times. The lens of this invention is a small diameter symmetrical double aspheric lens whose coaxial surfaces are of decreasing curvature from the apices peripheralward with the sum of the axial dioptric powers of the front and back surfaces ranging from 60 diopters to 130 diopters. The design of the surfaces of the lens is such that a flat aerial image of the fundus of the eye is formed from the light emerging from the eye in which aberrations including field curvature, astigmatism, and distortion are corrected.

10 Claims, 9 Drawing Figures

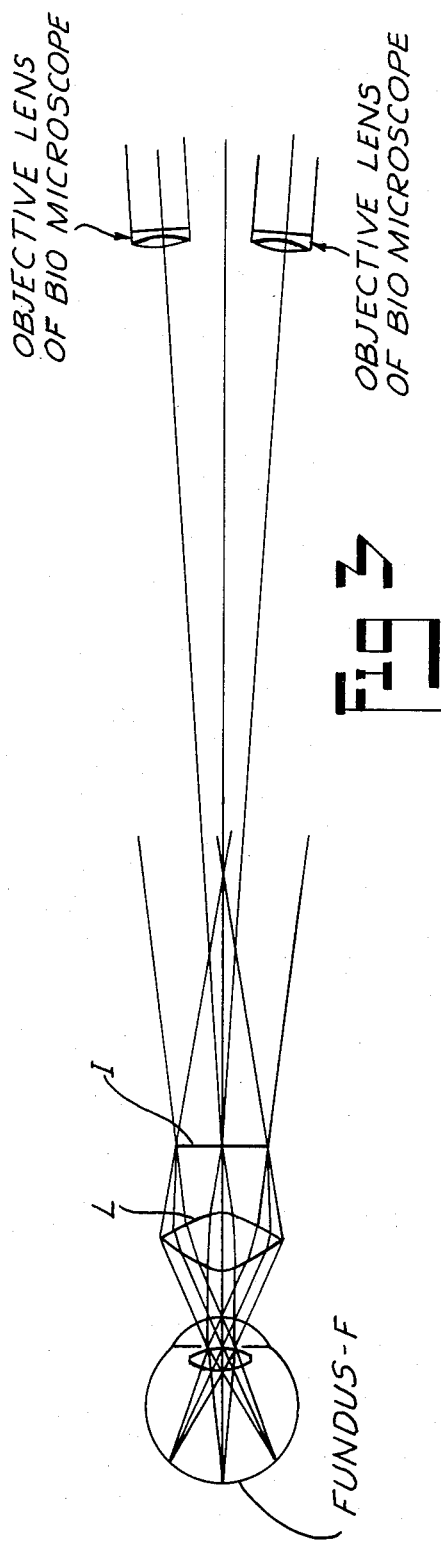
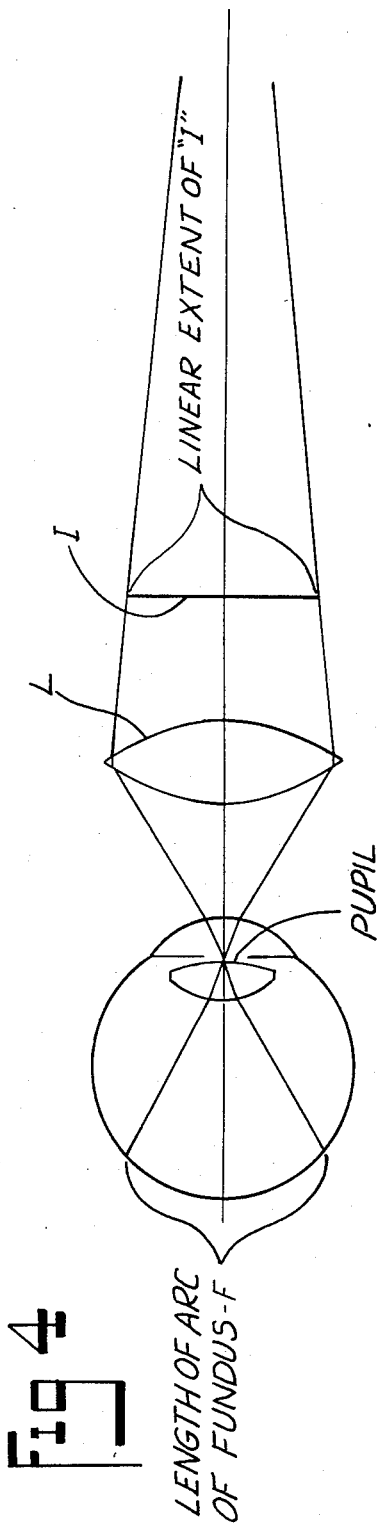

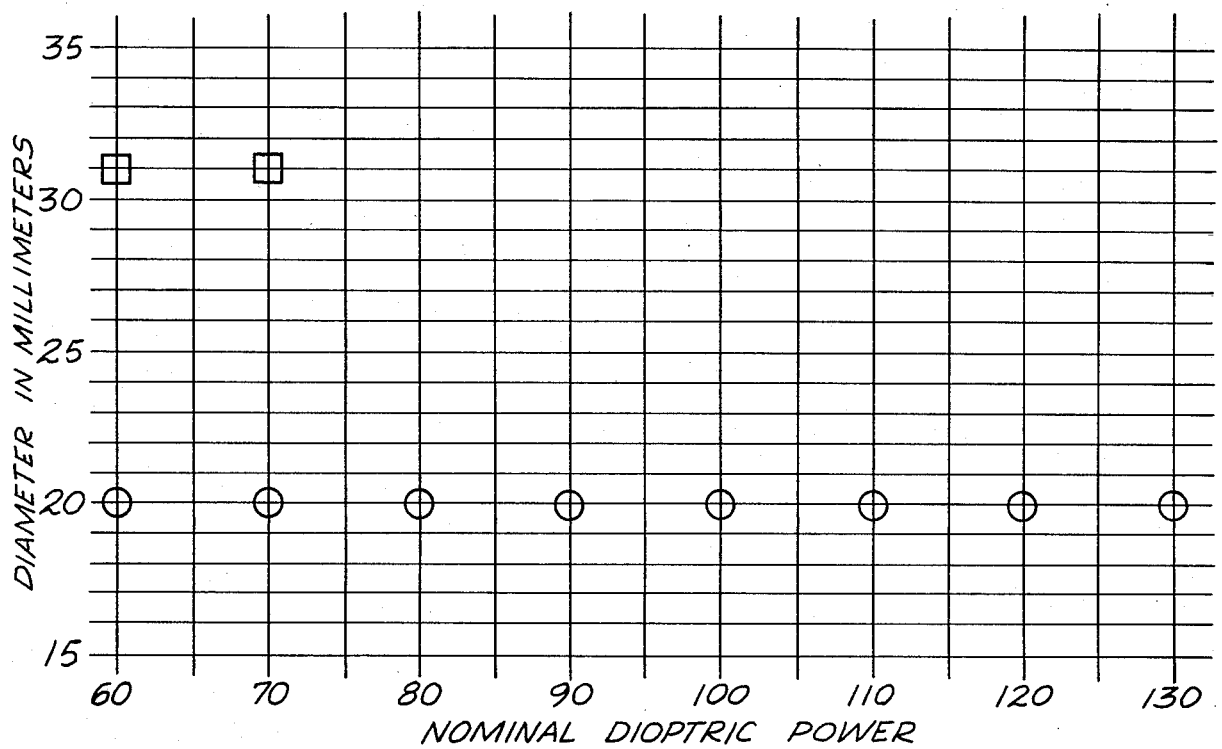
Fig 5
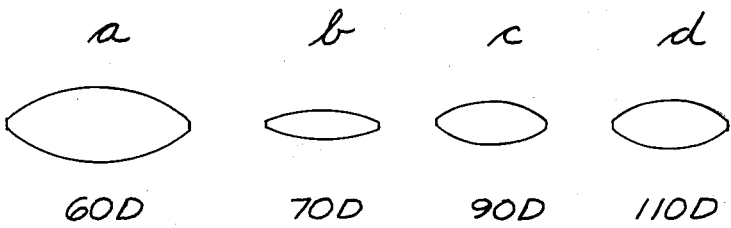
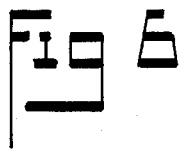
Fig 6

INDIRECT OPHTHALMOSCOPY LENS FOR USE WITH SLIT LAMP BIOMICROSCOPE

This invention relates to an improvement in an optical lens of homogeneous transparent glass or plastic for indirect ophthalmoscopy, which lens has two functions: firstly, as a condensing lens converging light from the light source of a slit lamp biomicroscope to the entrance pupil of the eye and thereby illuminating the fundus of the eye, and secondly and simultaneously, utilizing the light emerging from the eye, as an image forming lens which forms an inverted aerial image of the fundus of the eye, which image is viewed monocularly or binocularly and stereoscopically with the binocular biomicroscope of the slit lamp. The novel features of the lens of this invention are that both the front and back mathematically defined surfaces of the lens are identical positive very strong aspheric surfaces of revolution of decreasing curvature from their apices peripheralward having an apical umbilical point at which the derivative of curvature vanishes, on a common axis of revolution, the dioptric power at the apex of both front and back surfaces of the lens being equal, and the design of the lens being such that in use the lens converges the light from the slit lamp source toward an image of said source at the entrance pupil of the eye and thence diverging to illuminate the fundus of the eye, and simultaneously the lens forms with the light emerging from the eye a flat aerial image of the fundus of the eye in which the aberrations of the image including field curvature, astigmatism, and distortion are optimally corrected.

BRIEF DESCRIPTION OF THE DRAWINGS

FIG. 3 is a schematic representation of the observing system for viewing the aerial image I of the fundus F shown in FIG. 2 and as produced by the novel lens L of this invention showing the objective lenses of the binocular biomicroscope of the slit lamp.

FIG. 4 is a schematic scale drawing of a meridian section of an emmetropic eye and a properly positioned 90 diopter novel lens of this invention, showing the length of arc of the fundus corresponding to the linear extent of the aerial image of the fundus.

FIG. 5 is a graph showing the range of nominal dioptric powers of the novel lens of this invention for large and small diameter lenses and several exemplary lenses of recommended or preferred lens powers and diameters.

FIGS. 6a, 6b, 6c, and 6d are full scale drawings of a series of four novel indirect ophthalmoscopy lens of this invention of increasing power: in sequence; a 60 diopter 31 mm diameter lens; a 70 diopter 20 mm diameter lens; a 90 diopter 20 mm diameter lens, and a 110 diopter 20 mm diameter lens.

Figure 1:
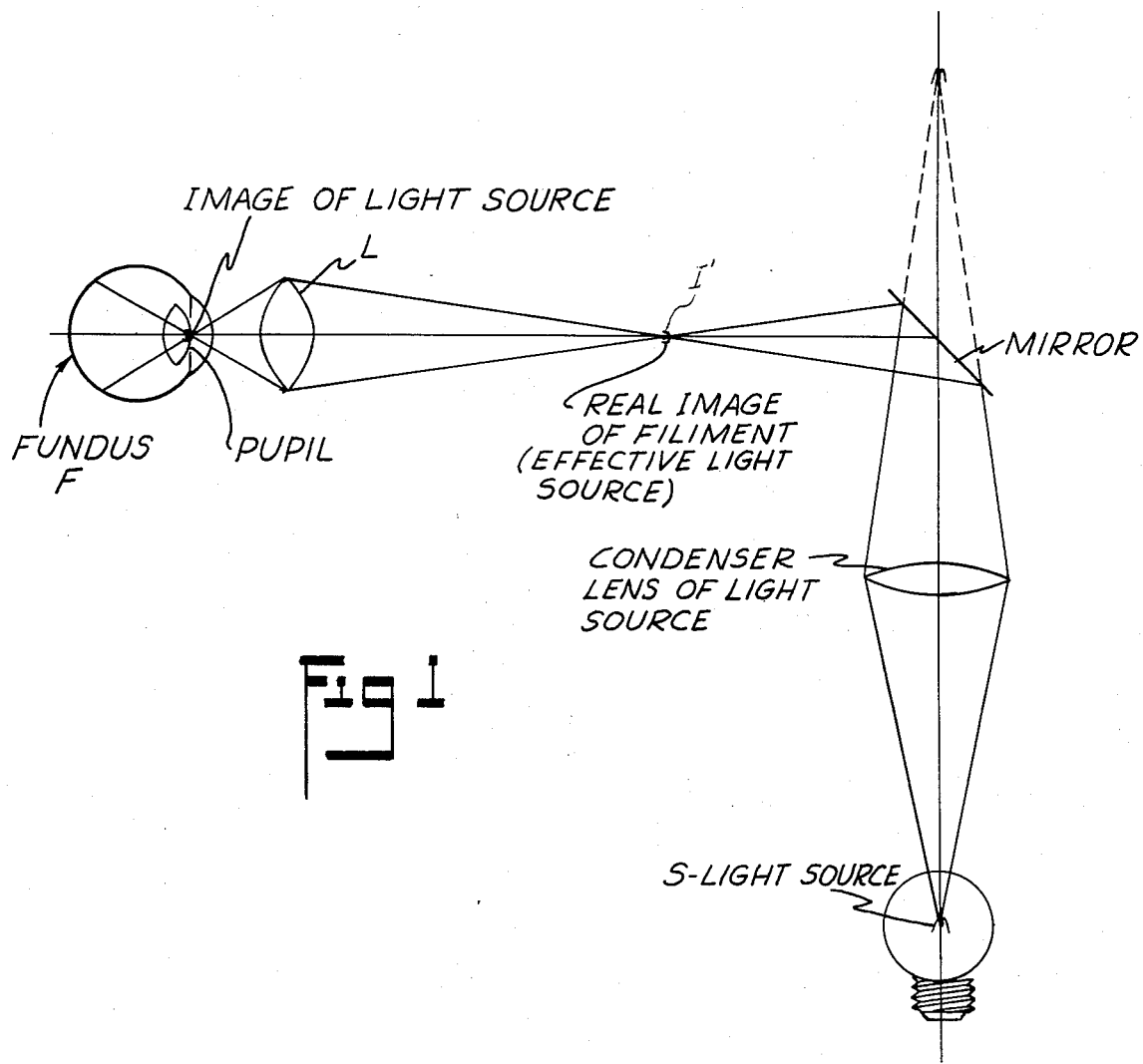
FIG. 1 is a schematic illustration of the illuminating system of the slit lamp biomicroscope, and the novel indirect ophthalmoscopy lens of this invention identified at L focusing the light towards the entrance pupil of the eye and thence illuminating the fundus F of the eye.

Table 1 lists the nominal powers of the total series of novel lenses of this invention, and the corresponding central thicknesses, effective diameters, and the equal front and back focal distances.

Table 2 lists the nominal powers of the series of novel lenses of this invention listed in Table 1 and the angular extent of the visual field subtended by the effective diameter of the novel lens at the entrance pupil of the eye and the magnification of the aerial image of the fundus.

PRIOR ART

In 1953, George El Bayadi first described the use of a +55 diopter lens with plane and spherical surfaces for use with the biomicroscope for examination of the fundus of the eye (British Journal of Ophthalmology, 37:625 1953).

In 1956, Hans Rotter described the use of a +58.6 diopter spherical lens for examining the posterior part of the vitreous cavity and the fundus of the highly myopic eye (American Journal of Ophthalmology, Vol. 42, No. 3, 409–415, September 1956).

In 1959, Emanuel Rosen described the use of a +55 diopter lens in conjunction with the slitbeam binocular biomicroscope for indirect ophthalmoscopy (American Journal of Ophthalmology, Vol. 48, No. 6, 783-787, December 1959).

In 1956 and again in 1957, David Volk exhibited conoid ophthalmic lenses at the annual meeting of the American Medical Association, Scientific Exhibits. The conoid lenses were composed of one conoid surface and one spherical or plano surface, and also composed of two conoid surfaces (AMA Scientific Exhibits, Grune and Straton 1957).

In 1958, Volk described conoid lenses in his paper "Conoid Refracting Lenses and Conoid Surfaces" (American Journal of Ophthalmology, Vol. 46, No. 1 part II, 86–95, July 1958). The conoid lenses had one or two conoid surfaces. In this paper Volk states, "Dr. R. David Sudarsky of the Eye Bank for Sight Restoration has found high powered conoid lenses to be of distinct advantage in indirect ophthalmoscopy, making possible the use of much stronger lenses and providing increased clearness and increased size of the field."

In 1959, Sudarsky and Volk reported their results on the use of conoid lenses for indirect ophthalmoscopy in their paper "Aspherical Objective Lenses as an Aid to Indirect Ophthalmoscopy" (American Journal of Ophthalmology, Vol. 47, No. 4, 572-575, April 1959). They evalulated a series of conoid lenses including a +60 diopter biconvex lens with both surfaces conoid.

In 1963, Volk reported on the use of conoid lenses for subnormal vision in his paper "Conoid Opthalmic Lenses in Legal Blindness" (American Journal of Ophthalmology, Vol. 56, No. 2, August 1963). The conoid lenses used consisted of a series of ten conoid lenses, the three strongest lenses each having two positive conoid surfaces.

In my copending patent application, "Lens For Indirect Ophthalmoscopy", U.S. Ser. No. 437,279, I have described an indirect ophthalmoscopy lens having both surfaces conoid on a common axis of revolution and wherein the two surfaces differ in dioptric power and shape. Nominal lens powers in said application range from 10 to 55 diopters.

In 1982, Volk introduced the +60Dsymmetrical Volk Conoid lens for indirect ophthalmoscopy especially for use in examination of the eyes of infants.

In 1984, Lundberg, in his paper, "Biomicroscopic Examination of the Ocular Fundus With a 60D Lens", reported on the use of the Volk Conoid 60 diopter lens with the slit lamp biomicroscope, citing the advantages of examining the aerial image of the fundus in this manner, especially the high magnification and wide field of view. This use of the +60DVolk Conoid lens in association with the slit lamp biomicroscope for detailed viewing of the fundus of the eye, markedly improved the examiner's ability to see details in the aerial image of the fundus.

Comments on Prior Art

In the prior art of El Bayadi, Rotter, and Rosen, the lens had spherical and plane surfaces which resulted in considerable aberrations in the aerial image of the fundus.

The +60 diopter symmetrical Volk Conoid lens, hereinafter called Volk Conoid lens, designed for subnormal vision and forming part of the investigation by Volk and Sudarsky for indirect ophthalmoscopy, was designed for subnormal vision and was found not to be as satisfactory for indirect ophthalmoscopy as lower powered lenses in the subnormal vision lens series.

The 60 diopter Volk Conoid lens for indirect ophthalmoscopy introduced in 1982 was useful for examination of the fundus of premature and full-term infants, but the use of conoid surfaces on this 60 diopter lens did not fully correct the optical aberrations. In addition, the aerial image of the fundus was only slightly magnified so that although said aerial image included a relatively large area of the fundus it was difficult to see details in said aerial image.

The use of the 60 diopter Volk Conoid lens in association with the slit lamp biomicroscope as described by Lundberg, was a marked improvement in the ability to see clearly and in detail the aerial image of the fundus of the eye as a consequence of the magnification of said aerial image by the biomicroscope. However, the 60 diopter Volk Conoid lens did not entirely meet the requirements in design for use with the slit lamp biomicroscope.

In the prior art of indirect ophthalmoscopy lenses as described in my copending patent application, "Lens For Indirect Ophthalmoscopy, U.S. Pat. No. 437,279, the indirect ophthalmoscopy lens had two different conoid surface. In the prior art 60 diopter Volk Conoid lens for indirect ophthalmoscopy, originally the 60 diopter Volk Conoid lens for subnormal vision, the lens had identical conoid front and back surfaces. When the same 60 diopter Volk Conoid lens was used for indirect ophthalmoscopy with the slit lamp beam of light could not be enlarged sufficiently to fill the full 29 mm aperture of the 60 diopter conoid lens, leaving a considerable portion of said lens unused as a condensing lens. Consequently, the extent of the fundus being illuminated was reduced. As a result, the aerial image of the fundus was likewise reduced in extent. In Addition, I determined that the 60 diopter conoid lens for indirect ophthalmoscopy could not fully correct for curvature of the field and lateral astigmatism using conoid surfaces. Full correction of the aberrations could only be achieved by surfaces other than conoids.

The novel lens of this invention differs from the 60 diopter Volk Conoid lens in several ways: it does not use conoid surfaces but instead uses mathematically definable surfaces which depart from conoids to reduce aberrations of the lens. The dioptric power of the lens surface at the apex is increased in power, ranging from 30 diopters to 65 diopters for each surface of the lens, with the nominal power of each lens being the sum of the dioptric power of its two identical surfaces; the diameter of the lens is reduced for more convenient handling by the examiner, the lens being held very close to the eye, the small size of the lens making it possible to avoid the side of the patient's nose during the examination. The illuminating system of the slit lamp differs from that of the indirect ophthalmoscope. See FIG. 1 which schematically illustrates the optics of the illuminating system of the slit lamp biomicroscope. Whereas the light source S reflected from the mirror of the indirect ophthalmoscope has a virtual source behind the mirror, that reflected from the slit lamp mirror is converged and forms a real aerial image I' of the slit lamp light source between the mirror and the novel condensing lens. The condensing lens then forms an image of said light source slightly behind the secondary focus of said lens, i.e., the light source and its image are conjugate. This illuminating system is quite different from that which is described in my copending patent application, "Lens for Indirect Ophthalmoscopy", U.S. Pat. No. 437,279, wherein the light source is at a sufficient distance from the condensing lens that a telecentric position of the condensing lens is quite close to the actual position of said condensing lens in the performance of indirect ophthalmoscopy. The novel lens of this invention must be so positioned in front of the patient's eye that the conjugate focus of the slit lamp light source is at or near the center of the entrance pupil of the patient's eye. Since said light source is relatively close to the novel lens, its conjugate focus is behind the secondary focus of said lens. Consequently, the lens must be positioned at a distance from the entrance pupil of the eye somewhat greater than the back focus of the lens in order that the conjugate focus of the slit lamp light source be at or near the center of the entrance pupil of the examined eye.

Figure 2:
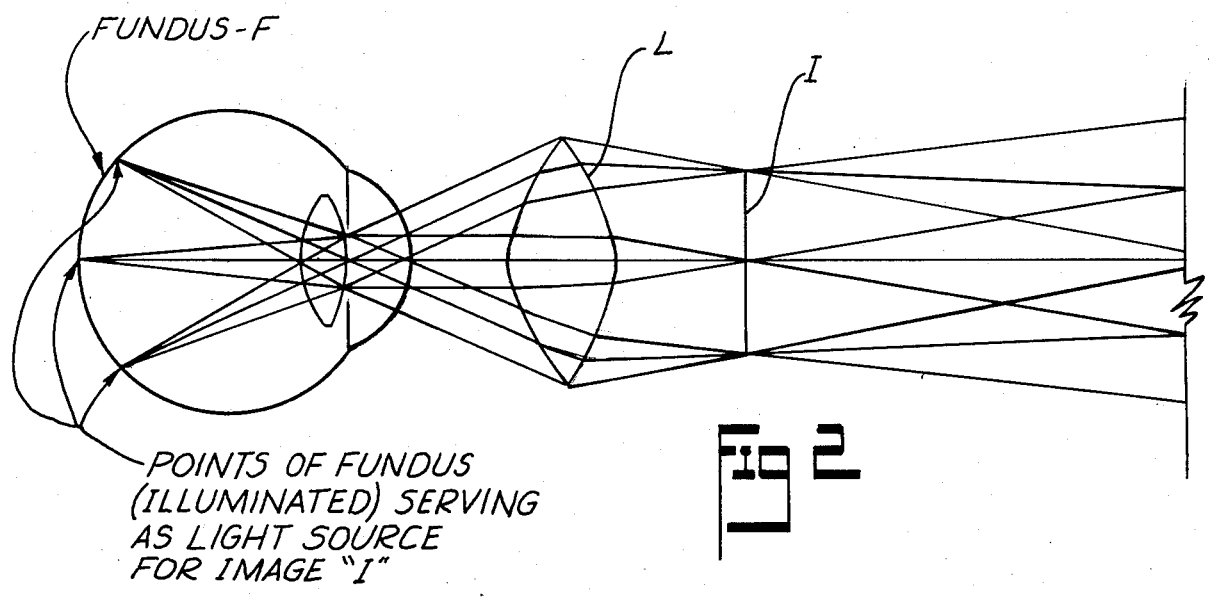
FIG. 2 is a schematic representation of the formation of the aerial image I by the novel lens of this invention of light emerging from the pupil of an emmetropic eye.

The design of said novel lens must take into account the two aspects of indirect ophthalmoscopy. It must converge the light from the slit lamp source to a relatively small image so that the light will pass through the pupil of the eye and illuminate the fundus, as shown in FIG. 1. Simultaneously, the novel lens must form a flat, clear undistorted inverted aerial image of the fundus of the eye between said novel lens and the biomicroscope with which said aerial image is viewed monocularly or binocularly and stereoscopically. FIG. 2 illustrates schematically the formation of said aerial image I by the novel lens L.

Of the two functions of the novel lens of this invention, condensing and image forming, that function of producing a sharp clear undistorted aberration-free image of the fundus takes precedence over its function as a condensing lens. Despite the fact that the novel aspheric lens of this invention is primarily designed to form an aberration-free aerial image of the fundus, the design is quite adequate for the function of condensing lens to focus the beam of light from the slit lamp light source toward a very small image of said source at the center of the entrance pupil of the eye. Generally indirect ophthalmoscopy with the slit lamp biomicroscope is performed with the pupil of the examined eye dilated, which permits all the light condensed by the novel lens to illuminate the fundus and which also improves the binocular stereoscopic viewing of the aerial image of the fundus with the biomicroscope. This is depicted in FIG. 3 which is a schematic drawing of the formation of the aerial image I of the fundus F by the light emerging from the eye, said drawing also showing the two objective lenses of the biomicroscope for viewing said aerial image binocularly and stereoscopically. I have taken the liberty in FIG. 3 of showing the formation of a single aerial image of the fundus, which would be the case for the viewing of the aerial image with a monocular biomicroscope, and have shown said single image as the object for the two objective lenses of the biomicroscope. There are in fact two closely positioned, overlapping slightly laterally displaced and slightly different aerial images, each of which corresponds to and is viewed with the corresponding eye of the examiner through the corresponding optics of the biomicroscope. It is the small differences in the two images as seen with the two eyes of the examiner which creates the retinal image disparity required for the stereopsis. Because of the difficulty in drawing the two separate aerial images and their formation from the light emerging from the eye, I have drawn only a single aerial image as representing the two images, and it should be understood that there is a distinct and separate aerial image for each half of the binocular biomicroscope.

MATHEMATICAL DESCRIPTION OF THE SURFACE OF THE NOVEL LENS OF THIS INVENTION

As already known in this art conoids or conicoids, including prolate ellipsoids, paraboloids, and hyperboloids of two sheets are specific types of surfaces of revolution whose meridian sections are conics, and are described mathematically by the following equation:

$$(1-e^2)x^2 - 2rx + y^2 = 0, \qquad (1)$$

where $r$ is the apical radius of curvature of the surface, which defines the magnitude of said surface, and $e$ is the eccentricity of the surface, which defines the shape of the surface, and where $x$ and $y$ are the Cartesian coordinates for points along the surface, the axis of the surface or its conic meridian section being the $x$ axis.

Equation 1 can be rewritten as:

$$y = (Ax + Bx^2)^{\frac{1}{2}}, \qquad (2)$$

where $A = 2r$ and $B = (e^2 - 1)$. Given the parameters, $r$ and $e$, $y$ can be determined for values of $x$ so that the coordinates of the entire surface can be defined for whatever interval of $x$ is desired.

The novel lens of this invention departs from conoids by adding additional terms to Equation 2, so that it becomes a polynomial in the following form:

$$y = (Ax + Bx^2)^{\frac{1}{2}} + Cx^p + Dx^q + Ex^z \ldots, \qquad (3)$$

where coefficients C, D, and E are integral or fractional coefficients, and where p, q and z are integral or fractional exponents.

In the novel lens of this invention, one or more of the additional terms in Equation 3 is utilized to produce the desired surfaces for a given lens. As an example, consider the novel lens having a nominal power of 90 diopters and a diameter of 20 mm and an edge thickness of 0.5 mm. Utilizing the following parameters: A=23.2 mm, B=1.1025, C=0.045, D=5.000, and E=0; p=1.05, and q=2.00, the surface produced results in the novel lens having a minimum of field curvature, a minimum of lateral astigmatism, and negligible distortion when used as the condensing image-forming lens for indirect ophthalmoscopy with the slit lamp biomicroscope. Said lens then has a central thickness of 7.71 mm and front and back focal distances of 9.68 mm, so that it is ideally suited for indirect ophthalmoscopy with the slit lamp biomicroscope. A scale drawing of said example lens in proper position in front of an emmetropic eye is shown in FIG. 4. Magnification of the aerial image as produced by the novel lens of this invention is defined as the ratio of the diameter of the aerial image of the fundus with respect to the length of arc of that portion of the fundus involved in the formation of said diameter of the aerial image. Magnification produced by the example 90 diopter novel lens used in conjunction with an emmetropic eye having a 7.7 mm apical radius of curvature and a length along its axis from the apex of the cornea to the inner surface of the sclera of 24.13 mm, and having a crystalline lens of 19 diopters, is 0.89.

In my research, I have determined that the range of nominal dioptric powers useful for slit lamp indirect ophthalmoscopy extends from 60 to 130 nominal diopters and have accordingly designed a series of said novel lenses at intervals of 10 diopters of power: for example, 70 diopters, 80 diopters, 90 diopters, etc. to a maximum of 130 diopters. Table 1 lists the nominal powers of the total series of novel lenses of this invention, and the corresponding central thicknesses, effective diameters, and the equal front and back focal distances. Table 2 lists the nominal powers of the series of novel lenses of this invention listed in Table 1 and the angular extent of the visual field subtended by the effective diameter of the novel lens at the entrance pupil of the eye and the magnification of the aerial image of the fundus. Included in Tables 1 and 2 are the characteristics of the 90 diopter novel lens depicted in FIG. 4 and used as the example lens in this specification. The data presented in Table 2, i.e., the angular extent of the field and magnification were calculated with respect to an emmetropic eye having a 7.7 mm apical radius of curvature, a length along the optical axis from the apex of the cornea to the inner surface of the sclera, 24.13 mm, and an intraocular lens of 19 diopters. From the data in Tables 1 and 2 it is seen that as a result of the increasingly shorter focal distance, the stronger the power of the lens, the closer it will be to the examined eye, the greater the extent of the field, and the lower the magnification of the aerial image.

The lower power lenses may be used to an advantage with myopic eyes, the greater the myopia, the weaker the lens power, while the stronger lenses may be used to an advantage with hypermetropic and aphakic eyes, the greater the hypermetropia the stronger the lens power, aphakia almost always being associated with strong hypermetropia. The use of the various powers of the novel lens of this invention in association with the corresponding refractive states of the examined eyes has the effect of maintaining the position of the aerial image of the fundus at or near a given vertical plane, thus requiring less to and fro movement of the slit lamp biomicroscope in adjusting its position to focus upon the aerial image for the various eyes. However, it is not essential that the lens correspond to various refractive errors of the eye; a given lens is quite satisfactory for use in normal and abnormal refractive states of the eye.

Each novel lens is preferably permanently mounted in a small metal ring for protection of the edge of the lens and to facilitate its handling. The edge of the ring may also be knurled to increase the holding ability of the examiner.

In FIG. 5, I have shown graphically the lens series. Small diameter 20 mm lenses are shown at 10 diopter intervals from 60 to 130 diopters while the larger diameter 31 mm lenses are shown only at the 60 and 70 diopter positions. The use of the small diameter for the higher power lenses is based on the fact that the strong lenses are held very close to the eye where the size of the nose could interfere with the positioning of the lens if its diameter were large. The use of the small diameter lens is also based on the fact that the width of the light source beam at the lens surface does not exceed the 18.5 mm effective diameter of the 20 mm diameter lens. I have found the lens diameters depicted in FIG. 5 very useful with the lenses being easily handled by the examiner. The symmetrical design of the lens is also an advantage in that the lens can be placed with either surface facing the patient. Although the lenses depicted in FIG. 5 are of the 31 mm and the 20 mm diameters, other diameters are also anticipated for the novel lens. Mounting of the lens in a ring slightly reduces the exposed lens surface since the lens is seated against a small shelf of about 0.75 mm width, so that the effective diameter of the 31 mm lens is about 29.5 mm, and that of the 20 mm lens is about 18.5 mm.

In FIG. 6, I have an exemplary set of four lenses 6(a–d) which may comprise a lens series for relative easy use by the examiner.

The novel indirect ophthalmoscopy lens of this invention is made of ophthalmic crown glass having an index of refraction n=1.523. Other types of glass having other indices of refraction may also be used and ophthalmic plastics may also be used for the novel lens of this invention. However, glass is preferred because of its resistance to scratching and because it can be very satisfactorily coated with durable antireflective materials to increase light transmission to better than 99% while at the same time reducing unwanted surface reflections to less than 1%. In addition to white or clear glass, which unrestrictedly transmits the entire visible spectrum, the novel lens of this invention is also made of transparent glass of various colors, and as in my copending patent application, "Lens For Indirect Ophthalmoscopy", U.S. Pat. No. 437,279, which includes: orange-red, which transmits almost exclusively light from the yellow-orange-red portion of the visible spectrum; yellow, which transmits almost exclusively light from the green-yellow-orange-red portion of the visible spectrum; and green, which transmits almost exclusively light from the green portion of the visible spectrum; and blue, which transmits almost exclusively light from the violet-blue and green-yellow portion of the visible spectrum.

Although the preferred method of using the novel lens of this invention is that it be hand-held in front of the examined eye, it may also be mounted in an adjustable holder to be positioned at any desired location in front of the examined eye.

TABLE 1

| Nominal Power of Lens (Diopters) | Effective Diameter (Millimeters) | Central Thickness (Millimeters) | Focal Distance (Milimeters) |
|---|---|---|---|
| 60 | 18.5 | 5.72 | 15.67 |
| 70 | 18.5 | 6.42 | 13.15 |
| 80 | 18.5 | 7.07 | 11.22 |
| 90 | 18.5 | 7.66 | 9.69 |
| 100 | 18.5 | 8.20 | 8.44 |
| 110 | 18.5 | 8.70 | 7.40 |
| 120 | 18.5 | 9.16 | 6.50 |
| 130 | 18.5 | 9.58 | 5.72 |
| 60 | 29.5 | 12.36 | 14.36 |

TABLE 1-continued

| Nominal Power of Lens (Diopters) | Effective Diameter (Millimeters) | Central Thickness (Millimeters) | Focal Distance (Milimeters) |
|---|---|---|---|
| 70 | 29.5 | 13.60 | 11.64 |

TABLE 2

| Nominal Power of Lens (Diopters) | Angular Extent of Field (Degrees) | Magnification of Aerial Image |
|---|---|---|
| 60 | 50° | 1.06 |
| 70 | 55° | .98 |
| 80 | 60° | .93 |
| 90 | 64° | .89 |
| 100 | 68° | .84 |
| 110 | 71° | .81 |
| 120 | 74° | .80 |
| 130 | 77° | .78 |
| 60 | 68° | 1.31 |
| 70 | 73° | 1.23 |

I claim:

1. A symmetrical biconvex aspheric indirect ophthalmoscopy lens of homogeneous transparent optical material for use with the slit lamp biomicroscope, each coaxial surface of said lens being a surface of revolution having an apical umbilical point at which the derivative of curvature vanishes, the magnitude and shape of each of the identical surfaces defined by the polynomial:

$$y = (Ax + Bx^2)^{\frac{1}{2}} + Cx^{(p)} + Dx^{(q)} + Ex^{(z)} \ldots,$$

where A is twice the apical radius of curvature of each surface, values of A ranging from about 20 mm to 7 mm, and B is $(e^2 - 1)$, e being the apical eccentricity of each surface with the value of e being within the range of 1.1 to 1.7, and C, D, and E are coefficients of successive terms in the polynomial, the range of values of each of said coefficients being from 0 to about 500 in integral or fractional amounts, and p, q, and z are exponents in said successive terms with values ranging integrally or fractionally from 0 to 8.

2. A lens as in claim 1 within the range of nominal powers from 60 to 130 diopters.

3. A lens as in claim 1 in which the homogeneous transparent optical material is glass.

4. A lens as in claim 1 in which the homogeneous transparent optical material is plastic.

5. A lens as in claim 1 of orange-red color in which the spectral transmission of the homogeneous transparent optical material is high and limited almost entirely to the yellow-orange-red portion of the visible spectrum.

6. A lens as in claim 1 of yellow color in which the spectral transmission of the homogeneous optical material is high and limited almost entirely to the green-yellow-orange-red portion of the visible spectrum.

7. A lens as in claim 1 of green color in which the spectral transmission of the homogeneous transparent optical material is high and limited almost entirely to the green portion of the visible spectrum.

8. A lens as in claim 1 of blue color in which the spectral transmission of the homogeneous transparent optical material is high and limited almost entirely to the violet-blue and green-yellow portions of the visible spectrum.

9. A lens as in claim 1 in which the homogeneous transparent optical material is fully transparent for the entire visible spectrum.

10. A series of lenses, each of which comes within the specification of claim 1, the range of nominal powers of the series extending from 60 diopters to 130 diopters, each lens in said series spaced at a given dioptric interval from adjacent lenses in said lens series.

* * * * *